United States Patent [19]

Yoshizumi et al.

[11] Patent Number: 5,319,194
[45] Date of Patent: Jun. 7, 1994

[54] APPARATUS FOR MEASURING BIREFRINGENCE WITHOUT EMPLOYING ROTATING MECHANISM

[75] Inventors: Keiichi Yoshizumi, Osaka; Keishi Kubo, Moriguchi, both of Japan

[73] Assignee: Matsushita Electric Industrial Co., Ltd., Osaka, Japan

[21] Appl. No.: 28,164

[22] Filed: Mar. 9, 1993

[30] Foreign Application Priority Data

Mar. 10, 1992 [JP] Japan .................................. 4-051114

[51] Int. Cl.⁵ .................................................. G02F 1/01
[52] U.S. Cl. ......................................... 250/225; 356/365
[58] Field of Search .......................... 250/225, 227.17; 356/364–368

[56] References Cited

U.S. PATENT DOCUMENTS

| | | | |
|---|---|---|---|
| 3,902,805 | 9/1975 | Redner | 356/365 |
| 4,179,217 | 12/1979 | Robert et al. | 356/365 |
| 4,629,323 | 12/1986 | Matsumoto | 356/365 |
| 4,749,854 | 6/1988 | Martens | 356/365 |
| 4,970,385 | 11/1990 | Tatsuno et al. | 250/225 |
| 5,102,222 | 4/1992 | Berger et al. | 356/365 |

FOREIGN PATENT DOCUMENTS

| | | | |
|---|---|---|---|
| 0210920 | 9/1986 | Japan | 356/365 |
| 0184444 | 7/1989 | Japan | 356/365 |
| 0218440 | 9/1991 | Japan | 356/365 |
| 4006444 | 1/1992 | Japan | 356/365 |

OTHER PUBLICATIONS

Modine et al., "High frequency polarization modulation method for measuring birefringence", Applied Optics, vol. 14, No. 3, pp. 757–760, Mar. 1975.
Chudakov, "Investigation of Induced Birefringence with a Rotation Polarization Element, Pribory; Telchnika Elesperimenta", No. 1, pp. 210–212, Jan. 1977.
Caldwell, "Digital Lock-in technique for measurement of polarization of radiation," Optics Letters, vol. 1, No. 3, Sep. 1977, pp. 101–103.
Norito Suzuki et al., Applied Optics 11, pp. 35–38, issued on Sep. 15, 1984 (Partial English Translation).
Etsuhiro Mochida, "Measurement of Birefringence by Phase Modulating Method and Application Thereof", Optical Technology Contact vol. 27, No. 3 (1989), pp. 129–131 (Partial English Translation).

*Primary Examiner*—David C. Nelms
*Attorney, Agent, or Firm*—Wenderoth, Lind & Ponack

[57] ABSTRACT

The birefringence of an object is measured by emitting first and second linearly polarized laser beams having optical frequencies f1 and f2 and transmitted in a same z-axis direction. The directions of polarization of the two laser beams are perpendicular to each other. After passing through the object, the laser beams are separated irrespective of the polarized directions thereof. A first analyzer transmits therethrough one of the laser beams that has been separated and polarized by about 45° with respect to the x-axis. A second analyzer transmits therethrough the other of the laser beams separated and polarized in the x-direction or y-direction. Respective photodetectors are provided for detecting the outputs of the first and second analyzers. The birefringence amount of the object and the direction of a lag-phase axis or of an advanced-phase axis is detected based on the outputs of the photodetectors and a difference in the frequencies f1 and f2 of the first and second laser beams.

3 Claims, 6 Drawing Sheets

APPARATUS FOR MEASURING BIREFRINGENCE WITHOUT EMPLOYING ROTATING MECHANISM

BACKGROUND OF THE INVENTION

The present invention relates to an apparatus for measuring the birefringence amount of a liquid crystal panel for use in a liquid crystal display, an optical component such as a glass plate or a lens having an oriented film attached thereto, or an optical disk, and its direction of a lag-phase axis at a speed as high as 0.002 seconds per point and with an accuracy as high as 0.01 nm. More particularly, the present invention relates to an apparatus for observing the distribution of fine molecules oriented by means of rubbing even though an electron microscope is incapable of doing so.

Analyzer-rotating method, phase compensating method, and phase modulating method have been used to measure a birefringence. According to the analyzer-rotating method, an object to be measured is placed behind a polarizer so that the direction of the birefringence forms an angle of about 45° with the polarization direction of the polarizer. An analyzer placed behind the object is rotated. A birefringence amount is calculated based on the maximum and minimum values of the output of a photodetector placed behind the analyzer.

According to the phase compensating method, the polarizer and the analyzer are placed with the axes thereof perpendicular to each other and an object to be measured is placed therebetween with the direction of the birefringence forming about 45°. A Babinet-Soleil compensator is interposed between the object and the analyzer and the Babinet-Soleil compensator is adjusted so that the amount of light which transmits through the object is minimum. The phase compensation amount indicated by the Babinet-Soleil compensator is the birefringence amount to be found.

These conventional methods are incapable of measuring a birefringence amount at a resolution smaller than nm (nanometer). The phase modulating method is capable of carrying out measurements at a higher resolution. According to the phase modulating method, laser beams which have been linearly polarized by about 45° with respect to an x-axis are phase-modulated in the x-axis by a photoelasticity modulator so as to find a birefringence amount based on the phase difference between the beat signal of the beam and the modulated signal thereof which has transmitted through the object.

The details of the phase modulating method is described in optical technology contact Vo. 27, No. 3 (1989) of "Measurement of birefringence by phase modulating method and application thereof" written by Etsuhiro Mochida. This method is capable of measuring a birefringence at a resolution as high as 0.01 nm.

None of the conventional methods are incapable of measuring the direction of the birefringence of the object, namely, the direction of an advance phase axis and that of a lag-phase axis and a birefringence amount. That is, none of the conventional methods are incapable of simultaneously measuring the difference between the phase of transmission light, the electric field of its light wave of which is in the direction of the advance phase axis and the phase of transmission light, the electric field of its light wave of which is in the direction of the lag-phase axis. Therefore, first, the direction of the birefringence is found by measuring the birefringence amount while the object is being rotated about the progress direction of light to be measured and then, the object is placed in the found direction of the birefringence. In this manner, the birefringence amount can be measured. It takes, however, more than a minute to measure the birefringence amount of one point including the period of time required for the rotation of the object.

It is necessary to rotate the object so as to measure the birefringence amount thereof and the direction of the birefringence. Therefore, in order to finely measure the distribution of the birefringence of an entire flat object surface, it is necessary to rotate the object in conformity with the direction of the birefringence at each point to be measured. As a result, the measuring period of time is long. In addition, if a point to be measured is not positioned at the rotational center, the point draws a circle. As a result, measurement errors occur.

SUMMARY OF THE INVENTION

It is an object of the present invention to provide an apparatus for measuring the degree of a birefringence and the direction of a lag-phase axis at a high speed.

It is an object of the present invention to provide an apparatus for measuring the distribution of an object which has a great area or cannot be rotated.

In accomplishing these and other objects, according to one aspect of the present invention, there is provided an apparatus for measuring a birefringence comprising: a light source for emitting onto an object a first linearly polarized laser beam, transmitted in a z-axis direction and having an optical frequency (f1), an optical electric field of which is in an x-axis direction, and a second linearly polarized laser beam, progressing along the same optical path as the first laser beam and having an optical frequency (f2), an optical electric field of which is in a y-axis direction perpendicular to the x-axis direction a difference cycle generating means for generating a difference cycle alternating signal of a difference frequency of f=f1−f2; an optical separating means for separating laser beams from the first and second laser beams which have transmitted through the object from each other at an approximate constant ratio irrespective of the polarized directions thereof; a first analyzer for transmitting therethrough only one of the laser beams separated by the optical separating means and polarized by about 45° with respect to the x-axis; a first photodetector for detecting the laser beam transmitted through the first analyzer; a second analyzer transmitting therethrough only an other beam of the laser beams separated by the optical separating means and polarized in the x-direction or the y-direction; a second photodetector for detecting the laser beam transmitted through the second analyzer; a multiplier for calculating a product (q) of a difference cycle alternating signal (f) and a signal (a) received and detected by the first photodetector and a product (s) of the difference cycle alternating signal (f) and a signal (b) received and detected by the second photodetector; and a calculating means for calculating a birefringence amount (d) of the object and a direction (c) of a lag-phase axis or that of an advance-phase axis based on the output of each of the multipliers.

According to the apparatus, a beam of light emitted by the light source transmits through the object and the beam which has transmitted through the object is divided into two beams. One of the beams passes through the first analyzer which transmits therethrough only a beam which is polarized by about 45° with respect to the x-axis and is received by the first photodetector to detect a signal (a) from the beam. The other beam passes through the second analyzer which transmits therethrough only a component polarized in the x-direction or the y-direction and is received by the second photodetector to detect a signal (b) from the beam. Based on the signal (a), the signal (b), and the difference cycle alternating signal (f), the multiplier outputs the product (q) of the signal (a) and the difference cycle alternating signal (f) and the product (s) of the signal (b) and the difference cycle alternating signal (f). In this manner, the birefringence amount (d) of the object and the direction (c) of the lag-phase axis are calculated.

If the transmittance of the object is not constant, a direct current component (T) of the signal (a) or that of the signal (b) is multiplied by a constant so as to find the transmittance of the object. A calculating equation for calculating the birefringence amount (d) of the object contains the direct current component (T).

The calculating equations are shown as follows:

$$d = \arcsin((q^2+s^2)^{\frac{1}{2}}/t), \text{ and}$$

$$c = \tfrac{1}{2}\arccos(-q/(q^2+s^2)^{\frac{1}{2}}) \text{ and}$$

$$c = \tfrac{1}{2}\arcsin(s/(q^2+s^2)^{\frac{1}{2}})$$

where $t = Ta_1^2 a_2^2$; $a_1$ and $a_2$ are the amplitude of the laser beam in each electric field; T is the transmittance of the object found by multiplying the direct current component by the constant; and c is found by satisfying both equations of c.

BRIEF DESCRIPTION OF THE DRAWINGS

These and other objects and features of the present invention will become clear from the following description taken in conjunction with the preferred embodiments thereof with reference to the accompanying drawings, in which.

DETAILED DESCRIPTION OF THE INVENTION

Before the description of the present invention proceeds, it is to be noted that like parts are designated by the like reference numerals throughout the accompanying drawings.

Figure 1:
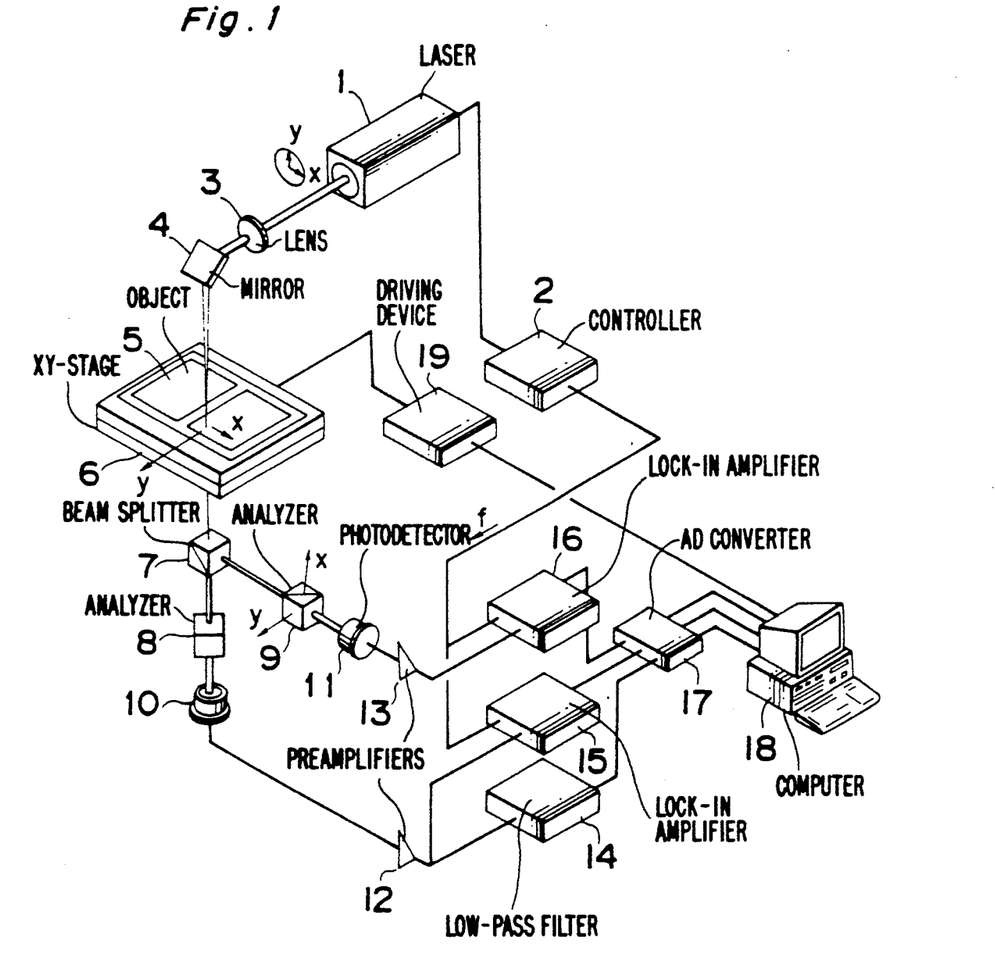
FIG. 1 is a block diagram showing the construction of an apparatus for measuring a birefringence according to an embodiment of the present invention.

Laser beams are emitted in a z-axis direction by an oscillation frequency-stabilized Zeeman laser 1 of He-Ne. The laser 1 emits a first linearly polarized laser beam, having a frequency of f1, the electric field of which is in an x-axis direction and a second linearly polarized laser beam, having a frequency of f2, the electric field of which is in a y-axis direction. In the laser 1, the energy levels of the two laser beams linearly polarized are slightly differentiated from each other by Zeeman effect when a magnetic field is applied to the laser pipe of the laser 1. As a result, the oscillation frequencies f1 and f2 are different from each other. The difference frequency (f) between the frequencies f1 and f2 can be outputted from the Zeeman laser 1 by a difference frequency means which is accommodated therein and outputs a difference cycle alternating signal of the difference frequency. The difference frequency (f) fluctuates unless the frequencies f1 and f2 are stabilized. In the oscillation frequency-stabilized Zeeman laser 1, the resonator length of the laser 1 is controlled to be constant so that the difference frequency (f) is constant. A fan is used to make a temperature constant in controlling the resonator length of the laser 1 or a piezoelectric element is attached to a resonator mirror to control the resonator length of the laser 1. The value of the difference frequency (f) ranges from 100 KHz to several MHz.

A controller 2 of the Zeeman laser 1 outputs a reference beat signal of the difference frequency (f). A lens 3 and a mirror 4 condense the Zeeman laser beams on an object 5 to be measured. The object 5 can be moved in the xy-directions by an xy-stage 6 driven by a driving device 19 controlled by a computer 18. The laser beam which has passed through the object 5 is divided into two by a non-polarized beam splitter 7 serving as a means for separating both beams having the frequencies f1 and f2. One of the beams passes through an analyzer 8 which transmits therethrough only a beam polarized by about 45° with respect to the x-axis and is received by a photodetector 10. The other beam passes through an analyzer 9 which transmits therethrough only a beam polarized in the x-direction or the y-direction and is received by a photodetector 11. It is to be noted that each progress direction of the beams is set as the z-axis direction.

Each of the photodetectors 10 and 11 detects a signal which changes according to the optical transmittance of the object 5, the birefringence amount thereof, and the direction of a lag-phase axis. The output (a) of the photodetector 10 passes through a low-pass filter 14, via a preamplifier 12, which detects only a direct current component (T) of the output (a) and a lock-in amplifier 15 which outputs the product (q) of an alternating current component of the output (a) and a reference signal (f) after it is rectified. The output (b) of the photodetector 11 passes through a lock-in amplifier 16, via a preamplifier 13, which outputs the product (s) of an alternating current component of the output (b) and a reference signal (f) after it is rectified.

The signals (T), (q), and (s) are AD-converted by an AD converter 17. Then, the converted signals are sent to the computer 18. The computer 18 calculates the birefringence amount and the direction of the lag-phase axis based on the signals (T), (q), and (s) as follows.

A complicated change occurs in the polarization state when beams pass through a polarizing element. The electric field of light is expressed in complex numbers by using Jones vector, and the object and the polarizing element are expressed by means of Jones matrix so as to perform calculations. In this manner, the birefringence amount of the object and the direction of the lag-phase axis can be correctly found.

The calculating method to be carried out by Jones matrix is described on page 35 of "Applied Optics II" written by Mr. Norito Suzuki et al. and published by Asakura Shoten, in 1982.

Let it be supposed that the Zeeman laser 1 oscillates at an oscillation angular frequency $\omega_1$ in the x-direction and $\omega_2$ in the Y-direction. Supposing that the amplitude in each direction is $a_1$ and $a_2$, the electric field $E_0$ of the laser beam is expressed in Jones vector as follows:

$$E_0 = \begin{bmatrix} E_x \\ E_y \end{bmatrix} = \begin{bmatrix} a_1 \exp(i\omega_1 t) \\ a_2 \exp(i\omega_2 t) \end{bmatrix}$$

Using (d) for the birefringence amount of the object; (c) for the direction of the lag-phase axis thereof; and (T) for optical transmittance thereof, Jones vector (P) regarding the object is as follows:

$$P = T^{\frac{1}{2}} \begin{bmatrix} \cos c & -\sin c \\ \sin c & \cos c \end{bmatrix} \begin{bmatrix} \exp(id) & 0 \\ 0 & 1 \end{bmatrix} \begin{bmatrix} \cos c & \sin c \\ -\sin c & \cos c \end{bmatrix}$$

Jones matrix $K_1$ of the analyzer 8 placed at about 45° with respect to the x-axis is expressed as follows:

$$K_1 = 1/2 \begin{bmatrix} 1 & 1 \\ 1 & 1 \end{bmatrix}$$

Jones matrix $K_2$ of the analyzer 9 placed in the x-axis direction is expressed as follows:

$$K_2 = \begin{bmatrix} 1 & 0 \\ 0 & 0 \end{bmatrix}$$

The vector $E_1$ in the electric field at the position of the photodetector 10 is expressed as follows:

$$E_1 = K_1 \cdot P \cdot E_0$$
$$= \begin{bmatrix} E_{1x} \\ E_{1y} \end{bmatrix}$$
$$= 1/2 \begin{bmatrix} 1 & 1 \\ 1 & 1 \end{bmatrix} T^{\frac{1}{2}} \begin{bmatrix} \cos c & -\sin c \\ \sin c & \cos c \end{bmatrix} \begin{bmatrix} \exp(id) & 0 \\ 0 & 1 \end{bmatrix}$$
$$\begin{bmatrix} \cos c & \sin c \\ -\sin c & \cos c \end{bmatrix} \begin{bmatrix} a_1 \exp(i\omega_1 t) \\ a_2 \exp(i\omega_2 t) \end{bmatrix}$$

$E_{1x} = 1/2 T^{\frac{1}{2}}((\exp(id)\cos^2 c + \sin^2 c)$ $a_1\exp(i\omega_1 t) + (\exp(id)\cos c \sin c - \cos c \sin c)$ $a_2\exp(i\omega_2 t) + (\exp(id)\sin c \cos c - \cos c \sin c)$ $a_1\exp(i\omega_1 t) + (\exp(id)\sin^2 c + \cos^2 c)a_2\exp(i\omega_2 t))$ $E_{1y} = E_{1x}$ The vector $E_2$ of the electric field at the position of the photodetector 11 is expressed as follows:

$$E_2 = K_2 \cdot P \cdot E_0$$
$$= \begin{bmatrix} E_{2x} \\ E_{2y} \end{bmatrix}$$
$$= \begin{bmatrix} 1 & 0 \\ 0 & 0 \end{bmatrix} T^{\frac{1}{2}} \begin{bmatrix} \cos c & -\sin c \\ \sin c & \cos c \end{bmatrix} \begin{bmatrix} \exp(id) & 0 \\ 0 & 1 \end{bmatrix}$$
$$\begin{bmatrix} \cos c & \sin c \\ -\sin c & \cos c \end{bmatrix} \begin{bmatrix} a_1\exp(i\omega_1 t) \\ a_2\exp(i\omega_2 t) \end{bmatrix}$$

-continued $E_{2x} = T^{\frac{1}{2}}((\exp(id)\cos^2 c + \sin^2 c)a_1\exp(i\omega_1 t) +$ $(\exp(id)\cos c \sin c - \cos c \sin c)a_2\exp(i\omega_2 t)$ $E_{2y} = 0$ The optical intensity at the position of the photodetector 10 is expressed in the product of the amplitude of the electric field and the complex conjugate thereof. The optical intensity $I_1$ which is a signal component capable of being detected by the photodetector 10 is expressed as shown by the following equation (1). The component of the optical frequency which cannot be detected by the photodetector 10 is removed from the calculated product of the amplitude of the electric field and the complex conjugate thereof.

$$I_1 = E_1 \cdot E_1^* = (E_{1x} + E_{1y})(E_{1x} + E_{1y})^* \quad (1)$$
$$= T[a_1^2\{1 + 1/2(1 - \cos d)\sin 4c\}/2 +$$
$$a_2^2\{1 - 1/2(1 - \cos d)\sin 4c\}/2 +$$
$$a_1a_2(\sin^2 2c\cos\omega t + \cos^2 c\cos d\cos\omega t -$$
$$\cos 2c\sin d\sin\omega t)]$$

In the above equation, $\omega_1 - \omega_2 = \omega$.

Similarly, the optical intensity $I_2$ which is detected by the photodetector 11 is expressed as follows:

$$I_2 = E_1 \cdot E_1^* \quad (2)$$
$$= T[a_1^2\{1 - 1/2(1 - \cos d)\sin^2 2c\} +$$
$$a_2^2 1/2(1 - \cos d)\sin^2 2c +$$
$$1/2a_1a_2(1 - \cos d)\sin 4c\cos\omega t +$$
$$a_1a_2\sin d\sin 2c\sin\omega t]$$

The amplitude of the cosine reference signal is shown as follows by substituting zero for (c) and (d) in equation (1):

$a_1^2 + a_2^2 + 2a_1a_2\cos\omega t$

The amplitude of the sine reference signal is represented as follows:

$a_1^2 + a_2^2 + 2a_1a_2\sin\omega t$

AC coupling of the reference signal is performed to remove DC component from the reference signal. Therefore, the intensity of the cosine reference signal and that of the sine reference signal are as follows:

$2a_1a_2\cos\omega t \quad (3)$ $2a_1a_2\sin\omega t \quad (4)$

The lock-in amplifiers 15, 16 output the product of (1) and (3), (1) and (4), (2) and (3), and (2) and (4).
The product (p) of (1) and (3) is as follows:

$p = Ta_1^2a_2^2(\cos^2 2c\cos d + \sin^2 2c) \quad (5)$

The product (q) of (1) and (4) is as follows:

$q = -Ta_1^2a_2^2\cos 2c\sin d \quad (6)$

The product (r) of (2) and (3) is as follows:
$$r = Ta_1^2 a_2^2 (1 - \cos d) \sin 4c / 2 \quad (7)$$

The product (s) of (2) and (4) is as follows:
$$s = ta_1^2 a_2^2 \sin 2c \sin d \quad (8)$$

Setting T $(a_1 a_2)^2 = t$, the following equation is obtained from equations (6) and (8):

$$\sin d = (q^2 + s^2)^{\frac{1}{2}} / t \quad (9)$$

The following equation is obtained from equations (6) and (9):

$$\cos 2c = -q/((q^2 + s^2)^{\frac{1}{2}}) \quad (11)$$

The following equation is obtained from equations (8) and (9):

$$\sin 2c = s/(q^2 + s^2)^{\frac{1}{2}} \quad (12)$$

The following equation is obtained from equations (5), (11), and (12):

$$\cos d = (p/t - s^2/(q^2 + s^2)) \, (4(q^2 + s^2))/q \quad (13)$$

The following equation is obtained from equations (7), (11), and (12):

$$\cos d = 1 + 2r(q^2 + s^2) t q s \quad (14)$$

The degree d (rad) of the birefringence of a sample and the direction (c) of the lag-phase axis are found by the equations based on the measured value of a point. The degree (d) of the birefringence of the sample is found from $\Delta n d \, (nm) = \lambda d/2\pi$. Only the detection of (q), (s), and (t) is necessary. That is, $$d = \arcsin\{(q^2 + s^2)^{\frac{1}{2}} / t\} \quad (15)$$

Figure 2:
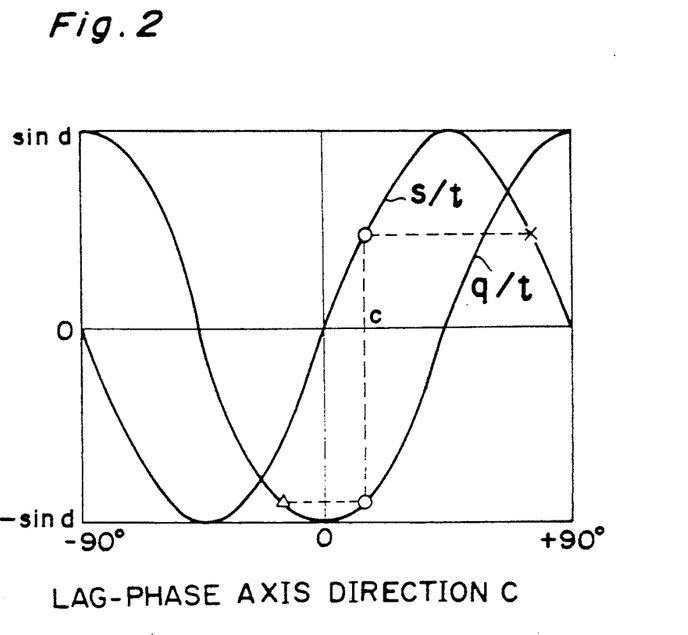
FIG. 2 is an explanatory view showing an equation for calculating a birefringence according to the embodiment of the present invention.

FIG. 2 is a graph showing q/t and s/t plotted when the direction (c) of the lag-phase axis is changed with the degree (d) of the birefringence fixed in equations (6) and (8). From the outputs of the lock-in amplifiers, q/t and s/t are obtained. The direction (c) of the lag-phase axis is obtained from equations (11) and (12) as follows:

$$c = \tfrac{1}{2}\arccos(-q/q^2 + s^2)^{\frac{1}{2}} \quad (16)$$

$$c = \tfrac{1}{2}\arcsin(s/(q^2 + s^2)^{\frac{1}{2}}) \quad (17)$$

That is, the direction (c) is found by satisfying both equations (16) and (17).

The direction (c) of the lag-phase axis has many solutions in 180° cycle. Therefore, FIG. 2 shows only ±90° which is physically significant. Values shown by a mark ◯ and a mark Δ are two solutions to the direction (c) because q/t is arccos, and values shown by a mark ◯ and a mark X are two solutions to the direction (c) because q/t is arcsin. A correct solution is the values shown by the mark ◯. That is, arcsin and arccos are equal to each other as shown in equations (16) and (17).

The direction of the advance-phase axis may be found instead of the direction of the lag-phase axis.

Figure 3:
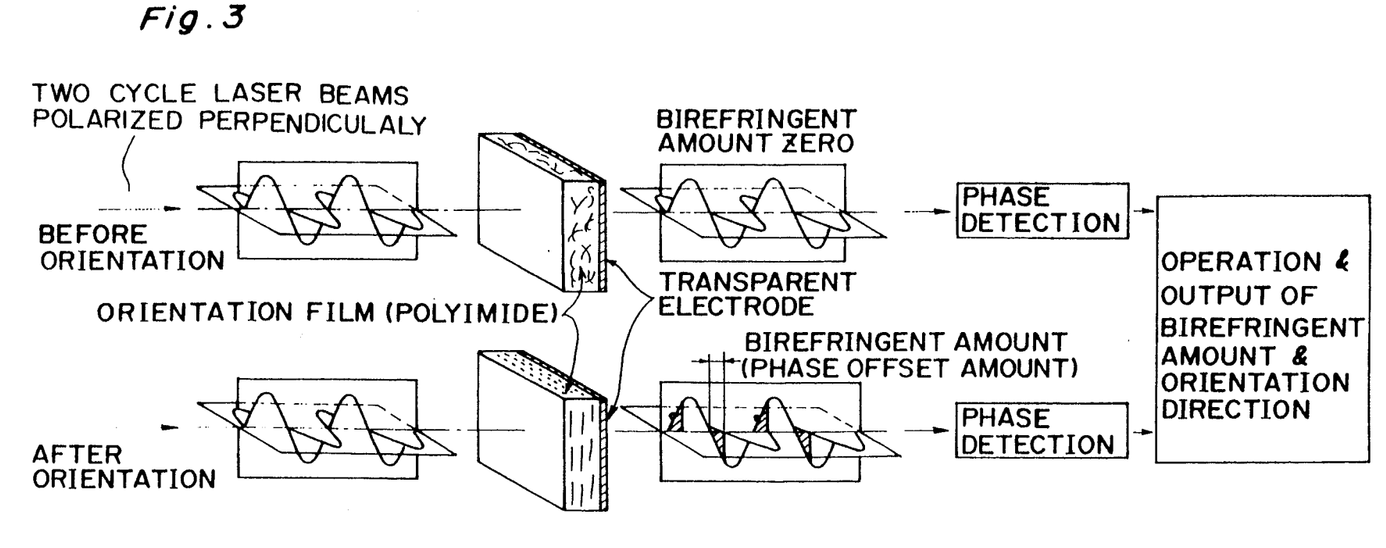
FIG. 3 is an explanatory view showing measurement of the birefringence of a liquid crystal panel.

FIG. 3 shows an example of measurement of the birefringence of a liquid crystal panel. Before orientation, two cycle laser beams polarized perpendicularly are transmitted through an oriented film made of polyimide and then the phase difference of the beams is detected. In this case, the birefringence amount is zero. The beams are incident to the film from one side opposing to the other side of a transparent electrode. After orientation formed by rubbing, the two cycle laser beams polarized perpendicularly are transmitted through the oriented film and then the phase difference of the beams is detected. In this case, the birefringence amount can be detected because the phases of the beams are shifted by the oriented film. The detected amount and the orientation direction are calculated and outputted.

A glass substrate has a birefringence distribution of 1-2 nm before rubbing. The birefringence is measured onto the glass substrate before and after rubbing. Then, the difference between the birefringence measured before and after rubbing is found by calculation so as to remove influence caused by the substrate. In the apparatus according to the embodiment, three thousand points can be automatically measured.

Figure 4A:
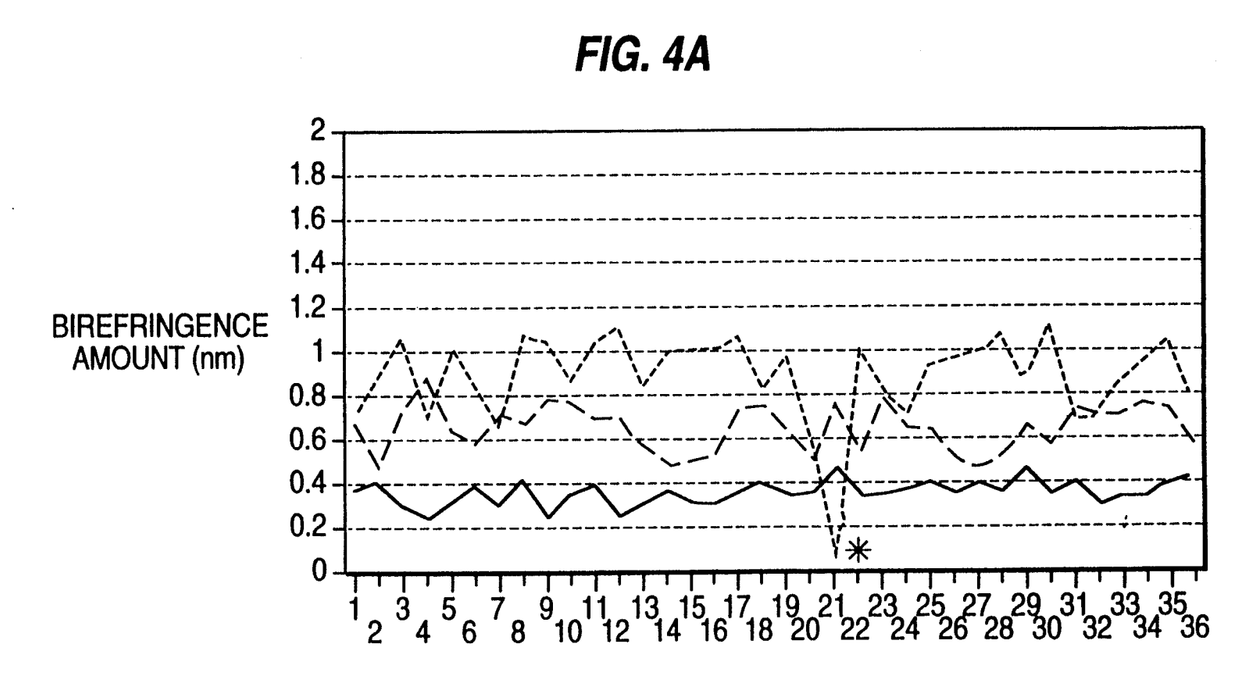
FIGS. 4A and 4B are, respectively, graphs showing a measurement example of the birefringence of an STN oriented liquid crystal panel.
Figure 4B:
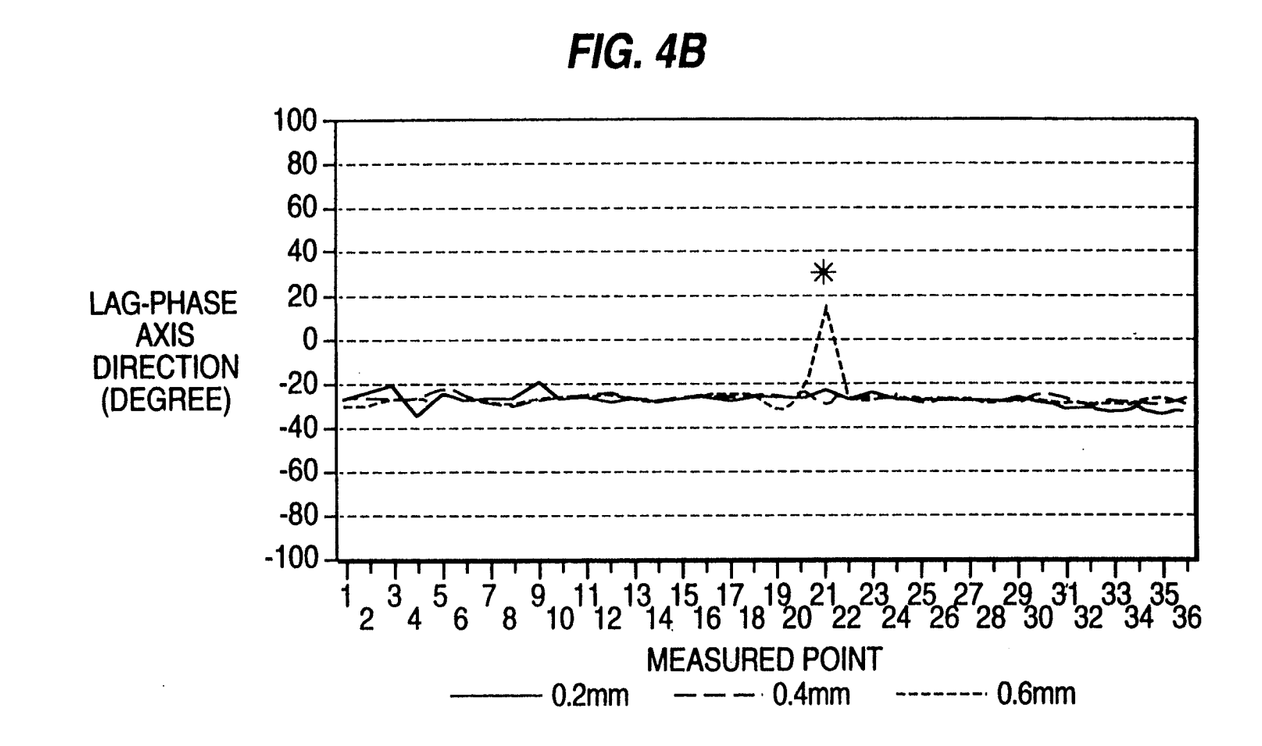

FIGS. 4A and 4B show a measurement example of a birefringence when the rubbing intensity of an STN liquid crystal is changed. As shown in FIGS. 4A and 4B, when the rubbing intensity is increased, the birefringence amount is increased and then the rubbing direction coincides with the lag-phase axis direction. That is, as shown in FIGS. 4A and 4B, the rubbing intensity of a liquid crystal panel is found from the birefringence amount thereof. In FIGS. 4A and 4B, in the rubbing process, when the push amount of the rubbing intensity is 0.6 mm, the rubbing failure can be found at the 21st measured point indicated by the mark *.

Figure 5:
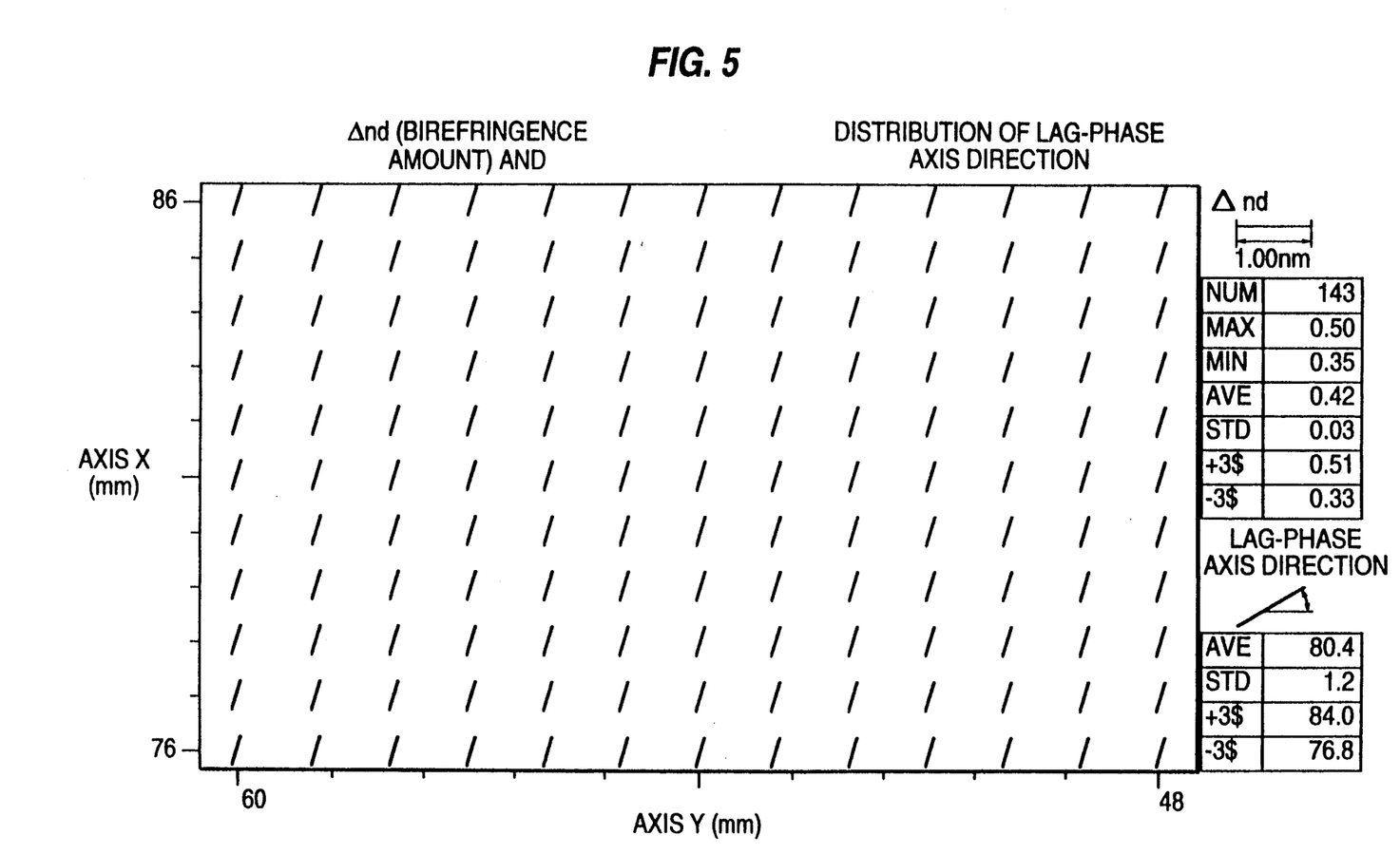
FIG. 5 is a graph showing a measurement example of the birefringence of a liquid crystal panel for color finder.

FIG. 5 shows a measurement example of a liquid crystal panel for a color finder of a VTR camera.

In the embodiment, the Zeeman laser is used as the light source for generating two cycles perpendicular to each other, but it is possible to use a laser which emits linearly polarized beams having a single waveform as previously described as the conventional example. A photoelasticity modulator or an AO modulator (Acousto-Optic Modulator) may be used to generate two cycles perpendicular to each other.

The apparatus according to the present invention is capable of simultaneously measuring the degree of the birefringence of the object to be measured and the direction of the lag-phase axis without rotating the object. Accordingly, the apparatus is capable of measuring them at a speed as high as 2 m sec per point. In addition, the apparatus is capable of easily measuring the distribution of the birefringence of an object which has a great area or cannot be rotated. The apparatus allows an operator to observe the distribution of molecules unlike conventional apparatuses.

Further, the apparatus is capable of measuring the birefringence of a liquid crystal panel, an oriented film, a lens, or an optical disk at a high speed with the apparatus finely scanning the entire surface of an object. Thus, the apparatus is capable of examining them during a process of a mass production thereof.

Although the present invention has been fully described in connection with the preferred embodiments thereof with reference to the accompanying drawings, it is to be noted that various changes and modifications are apparent to those skilled in the art. Such changes and modifications are to be understood as included within the scope of the present invention as defined by the appended claims unless they depart therefrom.

What is claimed is:

1. An apparatus for measuring a birefringence of an object, comprising:
- a light source for emitting onto the object a first linearly polarized laser beam, transmitted in a z-axis direction and having an optical frequency (f1), an optical electric field of which is an x-axis direction, and a second linearly polarized laser beam, progressing along the same optical path as the first laser beam and having an optical frequency (f2), an optical electric field of which is in a y-axis direction perpendicular to the x-axis direction;
- a difference cycle generating means for generating a difference cycle alternating signal of a difference frequency of $f=f1-f2$;
- an optical separating means for separating laser beams from the first and second laser beams which have transmitted through the object from each other at an approximate constant ratio irrespective of polarized direction thereof;
- a first analyzer for transmitting therethrough only one of the laser beams separated by the optical separating means and polarized by about 45° with respect to the x-axis;
- a first photodetector for detecting the laser beam transmitted through the first analyzer;
- a second analyzer for transmitting therethrough only an other beam of the laser beams separated by the optical separating means and polarized in the x-axis direction or the y-axis direction;
- a second photodetector for detecting the laser beam transmitted through the second analyzer;
- a multiplier for calculating a first product (q) of the difference cycle alternating signal (f) and a first signal (a) received and detected by the first photodetector and a second product (s) of the difference cycle alternating signal (f) and a second signal (b) received and detected by the second photodetector; and
- a calculating means for calculating a birefringence amount (d) of the object and a direction (c) of a lag-phase axis or that of an advance-phase axis based on the first product (q) and the second product (s) output from said multiplier.

2. The apparatus measuring a birefringence as claimed in claim 1, wherein the calculating means for calculating the birefringence amount (d) of the object comprises a low-pass filter for detecting a direct current component of the first signal (a) so that the direct current component is inputted into the calculating means.

3. The apparatus for measuring a birefringence as claimed in claim 2, wherein said calculating means includes means for calculating the birefringence amount (d) of the object and the direction (c) of the lag-phase axis based on the first product (q) and the second product (s) output from said multiplier in accordance with the following equations:

$$d = \arcsin\{(q^2+s^2)^{\frac{1}{2}}/t\|, \text{ and}$$

$$c = \tfrac{1}{2}\arccos(-q/(q^2+s^2)^{\frac{1}{2}}) \text{ and}$$

$$c = \tfrac{1}{2}\arcsin(s/(q^2+s^2)^{\frac{1}{2}})$$

where $t = T a_1^2 a_2^2$, where $a_1$ and $a_2$ are an amplitude of each of the laser beams in the electric fields, where T is a transmittance of the object corresponding to the direct current component multiplied by a constant, and where c is defined by satisfying both equations denoting c.

* * * * *